United States Patent [19]

De Kretser et al.

[11] Patent Number: 5,470,826

[45] Date of Patent: Nov. 28, 1995

[54] SINGLE CHAIN PROTEINS WITH FHS SUPPRESSING ACTIVITY ISOLATED FROM FOLLICULAR FLUID AND USES THEREOF

[75] Inventors: David M. De Kretser, Surrey Hills; Henry G. Burger, East Melbourne; Milton T. W. Hearn, Balwyn; David M. Milne-Robertson, Glen Waverley; Richard E. H. Wettenhall, Camberwell, all of Australia; Robert I. McLachlan, Seattle, Wash.; Fiona De Vos, Glen Waverley, Australia

[73] Assignees: Biotechnology Australia Pty Ltd., New South Wales; Monash University, Clayton; Monash Medical Centre, Melbourne; St. Vincents Institute of Medical Research, Fitzroy, all of Australia

[21] Appl. No.: 145,194

[22] Filed: Nov. 3, 1993

Related U.S. Application Data

[63] Continuation of Ser. No. 970,645, Nov. 2, 1992, abandoned, which is a continuation of Ser. No. 281,706, Nov. 29, 1988, abandoned.

[30] Foreign Application Priority Data

| | | | |
|---|---|---|---|
| Jan. 29, 1987 | [AU] | Australia | PI0081 |
| Jun. 17, 1987 | [AU] | Australia | PI2525 |
| Dec. 7, 1987 | [AU] | Australia | PI5765 |
| Dec. 7, 1987 | [AU] | Australia | PI5766 |

[51] Int. Cl.$^6$ .................. A61K 38/22; C07K 14/575
[52] U.S. Cl. .................. 514/8; 514/21; 530/397; 530/399; 530/850
[58] Field of Search .................. 514/8, 12, 21, 514/800; 530/397, 398, 399, 842, 850, 854

[56] References Cited

U.S. PATENT DOCUMENTS

| | | | |
|---|---|---|---|
| 4,215,130 | 7/1980 | Sjoerdsma | 514/392 |
| 4,585,754 | 4/1986 | Meisner et al. | 530/345 |
| 4,833,128 | 5/1989 | Solomon et al. | 514/909 |
| 5,037,805 | 8/1991 | Ling | 530/395 |
| 5,041,538 | 8/1991 | Ling et al. | 530/395 |

FOREIGN PATENT DOCUMENTS 00078  1/1986  WIPO.

OTHER PUBLICATIONS

Naoto Ueno, Nicholas Ling, Shao-Yao Ying, Frederick Esch, Shunichi Shimasaki, and Roger Guillemin, "Isolation and Partial characterization of Follistatin: A Single-Chain $M_r$ 35,000 monomeric protein that inhibits the release of follicle-stimulating hormone" Proc. Natl. Acad. Sci. USA, vol. 84, pp. 8282–8286, Dec. 1987.

Shao-Yao, Ann Becker, Geoff Swanson, Phil Tan, Nocholas Ling, Fred Esch, Naoto Ueno, Shunichi Shimasaki, and Roger Guillemin, "Follistatin Spcifically Inhibits Pituitary Follicle Stimulating Hormone Release In Vitro," Biochemical and Biophysical Research Communications, vol. 149, No. 1, 1987, Nov. 30, 1987, pp. 133–139.

D. M. Robertson, R. Klein, F. L. De Vos, R. I. McLachlan, R. E. H. Wettenhall, M. T. W. Hearn, H. G. Burger and D. M. de Krester, "The Isolation of Polypeptides with FSH Suppresing Activity from Bovine Follicular Fluid which are Structurally Different to Inhibin", Biochemical and Biophysical Research Communications, vol. 149, No. 2 1987, Dec. 16, 1987, pp. 744–749.

L. J. Leversha, D. M. Robertson, F. L. de Vos, F. J. Morgan, M. T. W. Hearn, R. E. Wettenhall, J. K.

(List continued on next page.)

Primary Examiner—Jeffrey E. Russel
Attorney, Agent, or Firm—Foley & Lardner

[57] ABSTRACT

Polypeptides exhibiting an inhibitory action over follitropin are disclosed. These polypeptides are designated follitropin suppressing proteins, or "FSP's," and range in size from 30 to 60 kD as determined by SDS-PAGE. Uses for FSP's, including regulation of fertility and as immunogens, are disclosed.

20 Claims, 5 Drawing Sheets

OTHER PUBLICATIONS

Findlay, H. G. Burger and D. M. de Krester, "Isolation of Inhibin from Ovine Follicular Fluid", 1987 Journal of Endocrinology Ltd. pp. 213–221.

Tsonis, C. G. & Sharpe, R. M., "Dual gonadal control of follicule–stimulating hormone", Nature (1986), 321, 724–725.

Robertson, D. M., de Vos, F. L., Foulds, L. M., McLachlan, R. I., Burger, H. G., Morgan, F. J., Hearn, M. T. W., & de Kretser, D. M., "Isolation of a 31kDa form of inhibin from bovine follicular fluid", Mol. Cell Endocrin. (1986), 44, 271–277.

Ling, N., Ying, S., Ueno, N., Shimasaki, S., Esch, F., Hotta, M. and Guillemin, R., "Pituitary FSH is released bvy a heterodimer of the B–subunits from the two forms of inhibin" Nature (1986), 321, 779–782.

Vale, W., Rivier, J., Vaughan, J., McClintock, R., Corrigan, A., Woo, W., Karr, D. & Spiess. J., "Purification & characterisation of an FSH releasing protein from porcine ovarian follicular fluid" Nature (1986), 321, 776–779.

Laemmli, U. K., "Cleavage of structural proteins during the assembly of the head of bacteriophage T4", Nature (1970) 227, 680–685.

Hunkapiller, M. W., Lujan, E., Ostrander, F. & Hood L., "Isolation of microgram quantities of proteins from polyacrylamide gels for amino acid sequence analysis", Methods in Enzymology (1983) 91, 227–236.

Zimmerman, C. L., Appella, E. & Pisano J. J., "Rapid analysis of amino acid phenylthiohydantoins by high–performance liquid chromatography", Analytical Biochemistry (1977), 77, 569–573.

Scott, R. S., Burger H. G. & Quigg, H. "A simple & rapid in–vitro bio–assay for inhibin", Endocrinology (1980), 107, 1536–1542.

McLachlan, R. I., Robertson, D. M., Burger, H. Q. & de Kretser, D. M. "The radioimmunossay of bovine & human follicular fluid & serum inhibin", Mol. Cell. Endocrin. (1986), 46, 175–185.

McLachlan, R. I., Robertson, D. M., Healy, D. L., Burger, H. G. & de Kretser, D. M., "Circulating immunoreactive inhibin levels during the normal human menstrual cycle" J. Crin. Endocrin (1987), 65, 5, 954–961.

McLachlan, R. I., Robertson, D. M., de Kretser, D. M. & Burger H. O., "Inhibin–a non–steroidal regulator of pituitary follicle stimulating hormone", Baillere's Clinical Endorinology & metobolism (1987) 1,1, 89–112.

Roberts, A. B., Sporn, M. B., "Transforming growth factors", Cancer Surveys (1985), 4,4, 683–705.

Cate, R. L., Mattaliano, R. J., Hession, C., Tizard, R., Forbes, N. M. Cheng, A., Ninta, E. G., Frey, A. Z., Gash, D. J., Chow, E. P., Fisher, R. A., Bertonis, J. M., Torres, G., Wallner, B. P., Ramacharndran, K. L., Ragin, R. C., Manganaro, T. F., McLaughlin, D. T. & Donohoe, P. K., "Isolation of the bovine & human genes for Mullerian inhibiting sustance & expression of the human gene in animal cells" Cell. (1986), 45, 688–698.

Kauppila, K., Cantell, K., Janne, O., Kokko, E., & Vihko, R., "Serum sex steroid & peptide hormone concentrations & endometrial estrogen & progestin receptor levels during adminastration of human leucocyte interferon" Intl. J. Cancer (1982), 29, 291–294.

Orava, M., Cantell, K. & Vihko, K., "Human leukocyte interferon inhibits human chorionic gonadotropin stimulated testosterone production by porcine leydig cells in culture", Biochemical & Biophysical Research Communications (1985), 127, 3, 809–815.

Farnworth, P. G., Robertson, D. M., de Kretser, D. M. & Burger, H. G. "Effects of 31 kilodalton bovine inhibin on follicle stimulating hormone & luteinizing hormone in rat pituitary cells in vitro: Actions under basal conditions", Endocrinology (1988) 122, 1, 207–213.

REVERSED PHASE HPLC OF THE
HUMAN INHIBIN (PEAK II) AND HUMAN FSP

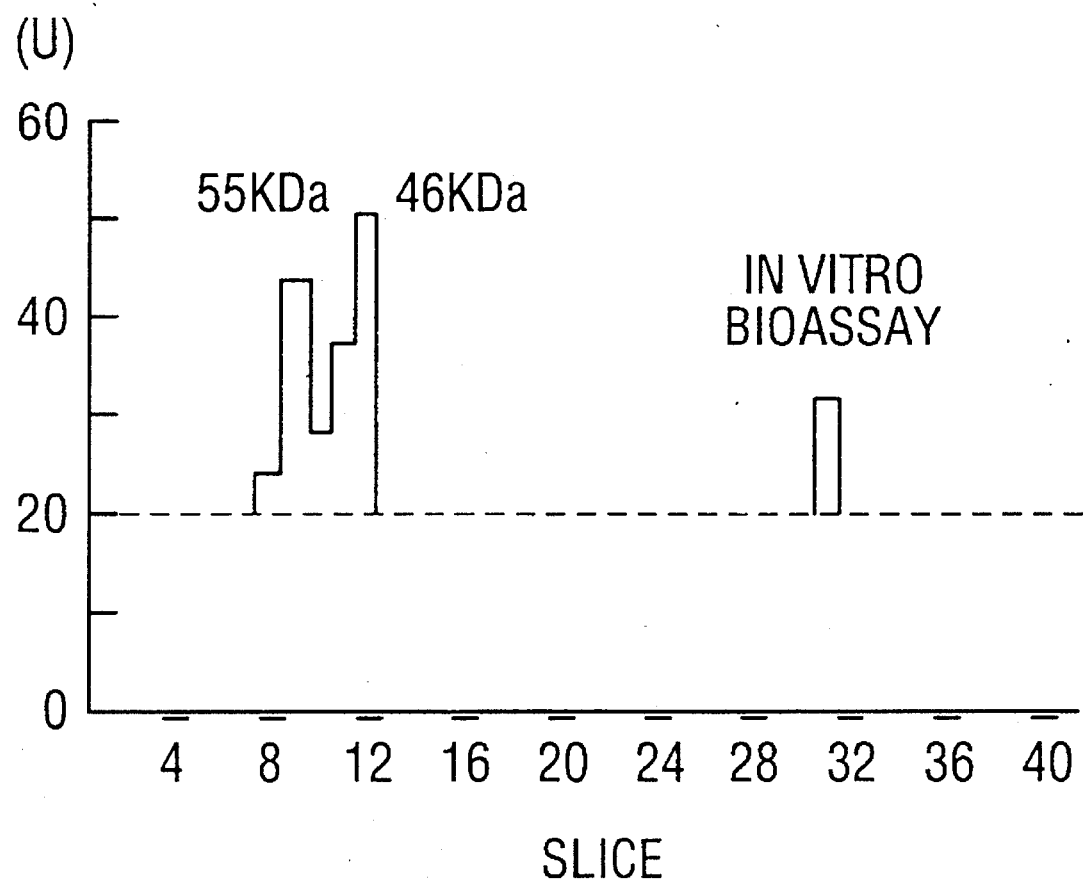

SINGLE CHAIN PROTEINS WITH FHS SUPPRESSING ACTIVITY ISOLATED FROM FOLLICULAR FLUID AND USES THEREOF

This application is a continuation of application Ser. No. 07/970,645, filed Nov. 2, 1992, now abandoned, which is a continuation of Ser. No. 07/281,706, filed Nov. 29, 1988, now abandoned.

TECHNICAL FIELD

The invention relates to the identification in follicular fluid of proteins with FSH-suppressing activity. These proteins can be distinguished from another class of molecules with FSH-suppressing activity, the inhibins, by their lack of reactivity in a specific radioimmunoassay, by their different molecular weight, $NH_2$ terminal amino acid sequence and absence of subunit structure.

BACKGROUND ART

The pituitary glycoprotein hormones, follitropin (FSH) and lutropin (LH), are known to be secreted in response to the hypothalamic releasing hormone GnRH. They act on the gonads which in turn product hormones that act as feedback inhibitors. The feedback inhibition of LH is almost entirely due to the action of gonadal steroids, whereas that of FSH is though to be due in part to the action of the gonadal glycoprotein hormone, inhibin, and in part to gonadal steroids.

Inhibin has recently been purified to homogeneity and its primary structure determined from gene sequencing. It is a member of a gene family which includes Mullerian inhibiting substance (MIS) and transforming growth factor-β (TGF-β). Inhibin is a heterodimer composed of an A or α subunit and a B or β subunit and in certain species, there are two types of β subunit designated $β_A$ and $β_B$ giving rise to $αβ_A$ and $αβ_B$ forms of inhibin.

Surprisingly, $β_A$ homodimers and $β_A β_B$ heterodimers were found to exist in follicular fluid and to have an effect opposite to that of inhibin. That is, they act to stimulate FSH synthesis and release and have been termed "activin" [Ling et al (1986) Nature 321 779–782] or "FRP" (FSH-releasing peptide) [Vale et al (1986) Nature 321 776–779]. An overview of the field is given by Tsonis and Sharpe (1986) Nature 321, 724–725.

The current invention provides the isolation of a second proteinaceous molecule with FSH-suppressing activity termed FSH-suppressing protein (FSP).

Since FSP can suppress FSH levels, FSP will be useful as a contraceptive agent in both sexes; in promoting fertility either by immunisation or by using the rebound effect in FSH levels following FSP administration; or as a diagnostic aid in monitoring gonadal function. However, it is to be noted that whilst this protein has been purified on the basis of its suppression of pituitary FSH production and named FSP, it does not exclude the fact that it may also have major activities (including those of growth factor/differentiation factor) other than that implied by its name. For example, MIS also acts as an oocyte meiosis inhibitor and TGF-β has an FRP/activin-like activity.

DESCRIPTION OF THE INVENTION

In a first embodiment the invention provides the isolation and characterisation of a unique series of proteins from follicular fluid having FSH suppressing activity termed FSP. They range from 30–60 kD as estimated from SDS-PAGE in the absence of reducing agents.

On isolation from bovine follicular fluid they have been further characterized as having identical $NH_2$-terminal amino acid sequences. They are distinct from inhibin based on $NH_2$-terminal amino acid sequence, molecular mass, absence of subunit structure, absence of inhibin immunoactivity and the failure of neutralizing inhibin anti-sera to neutralize their bioactivity in vitro. Their "inhibin-like" biological activities based on their ability to suppress FSH cell content of pituitary cells in culture are 5–10% that of bovine 31 kD inhibin, upon purification by the method herein described.

In one preferred form, the invention provides single chain proteins isolated from bovine follicular fluid (bFF) which have the capacity to suppress FSH secretion in vitro. The single chain proteins have apparent molecular weights of about 31 kD, about 35 kD and about 39 kD as determined by SDS-PAGE in the absence of reducing agents.

In a second preferred form, the invention provides single chain (glyco) proteins isolated from human follicular fluid (hFF) which have the capacity to suppress FSH secretion in vitro having molecular weights of between about 40 kD and about 60 kD and preferably of about 46 kD or about 55 kD as determined by SDS-PAGE in the absence of reducing agents.

It is recognized that it is possible to provide cleavage products, and synthetic equivalents thereof, of proteins of the invention which will maintain the biological or immunological activity of FSP. These cleavage products and synthetic equivalents will also be useful as contraceptive agents or as diagnostic aids in monitoring function.

It is also recognized that characterization of FSP including determination of its $NH_2$-terminal amino acid sequence provides the possibility of producing FSP by means other than purification from natural sources, as herein described. Such means include utilization of recombinant DNA techniques including cDNA techniques and/or other purification schemes.

The invention also provides a composition comprising at least one protein of the invention and a non-toxic carrier or diluent.

Compositions of the invention include those suitable for oral administration or in injectable form and preferably include a medically or veterinarily acceptable adjuvant. Also included in the compositions of the present invention are those in sustained release form, particularly suited for implantation and sustained release in a vertebrate. In such a form the composition can be implanted into a vertebrate to affect gonadal function and removed when the desired effect is obtained.

The invention also includes a method of affecting gonadal function in a vertebrate comprising administering to said vertebrate an effective amount of a composition of the present invention.

In a further form the invention embraces antibody preparations prepared as a result of immunological challenge to a vertebrate by administration of one or more proteins of the present invention or compositions of the present invention. Such antibody preparations include polyclonal and monoclonal antibody preparations. Such antibody preparations can be made as a result of administering proteins or compositions of the invention to a mammalian host by an appropriate route of immunication after emulsification with an appropriate diluent or adjuvant such as Freund's-type adjuvants or Marcol type adjuvants, and utilizing standard vaccination regimes. The antibodies so raised may be polyclonal or monoclonal in nature, this of course being dependent on the method of preparation used. Such antibodies may be used as diagnostic tools or used for passive administration to a host.

Throughout this specification and claims use of the term "FSP" is non-species specific and accordingly embraces related species of FSP such as bovine, human, ovine, porcine, equine, chicken and fish and particularly human and bovine FSP. Also the term embraces non-glycosylated and glycosylated FSP species.

The term "vertebrate" embraces species of fish, amphibians, reptiles, birds and mammals including humans.

The uses described in International patent application No. PCT/AU85/00119 for inhibin will also apply for FSP to the extent that inhibin and FSP have been shown to share biological activity.

The invention includes uses of FSP including: a method for suppressing FSH levels in a mammal; a method of raising FSH levels in a mammal; a method of increasing the ovulation rate of a female mammal; a method of increasing spermatogenesis in a male mammal; a method of reducing fertility in a male or female mammal; a method of advancing the onset of puberty in sexually immature male or female mammal; a method of delaying the onset of puberty or suppressing puberty in a male or female mammal; a method for treatment of precocious puberty; a method for the determination of the fertility status of a mammal; and a method for suppressing ovulation in a mammal, each of these methods comprising administration of a protein, composition, or antibody of the invention to the mammal as appropriate and at appropriate dosage. For instance suppression of ovulation will require administration of sufficiently high doses of FSP to suppress LH secretion.

The invention also encompasses methods for assaying FSP characterized by use of antibodies of the invention.

BRIEF DESCRIPTION OF THE DRAWINGS

Notwithstanding the above forms which fall within the broad form of the present invention, preferred forms of the invention will be further described with reference to the following experimental methodology and accompanying drawings wherein:

FIG. 5 preparative PAGE of human FSP. FSP-containing fractions obtained after RP-HPLC (See FIG. 4) were further fractionated on 10% PAGs followed by an electroelution step. FSH suppressing activity was determined in each fraction. In relation to protein standard markers (See FIG. 2). FSH suppressing activity was identified in the 40–60 kD region of the gel with peak activities found at 46 and 55 kD.

BEST MODES OF CARRYING OUT THE INVENTION

The following abbreviations are used in the text.
bFF : bovine follicular fluid
bFSP : bovine FSH suppressing protein
CG : chorionic gonadotropin
D : Dalton
DTT : dithiothreitol
EDTA : ethylenediaminetetraacetic acid
ELISA : enzyme-linked immunosorbent assay
FRP : FSH releasing peptide
FSH : Follitropin or follicle stimulating hormone
FSP : FSH suppressing protein x G : times the force due to gravity
g : gram
GnRH : Gonadotropin releasing hormone or LHRH
hFF : Human follicular fluid
hFSP : Human FSH suppressing protein
HPLC : high performance liquid chromatography
k : (prefix) kilo
l : litre
LH : Lutropin or luteinising hormone
LHRH : luteinising hormone releasing hormone
M : molar concentration
m : (prefix) milli
MIS : Mullerian inhibiting substance
mol : mole
MW : molecular weight
p : (prefix) pico
n : (prefix) nano
PAG : polyacrylamide gel
PAGE : polyacrylamide gel electrophoresis
PCMB : parachloromercuribenzoic acid
PMS : post-menopausal serum
PMSF : phenylmetnylsulfonylfluoride
PMSG : pregnant mares serum gonadotropin
RIA : radioimmunoassay
RP-HPLC : reversed phase HPLC
SDS : sodium dodecylsulfate
SS : steer serum
Tris : tris(hydroxymethyl)aminomethane
μ: (prefix)micro
wt : weight

EXAMPLE 1

THE ISOLATION AND CHARACTERISATION OF A PROTEIN FROM BOVINE FOLLICULAR FLUID (bFF) CALLED FSH SUPPRESSING PROTEIN(FSP)

General Methods

Figure 1A:
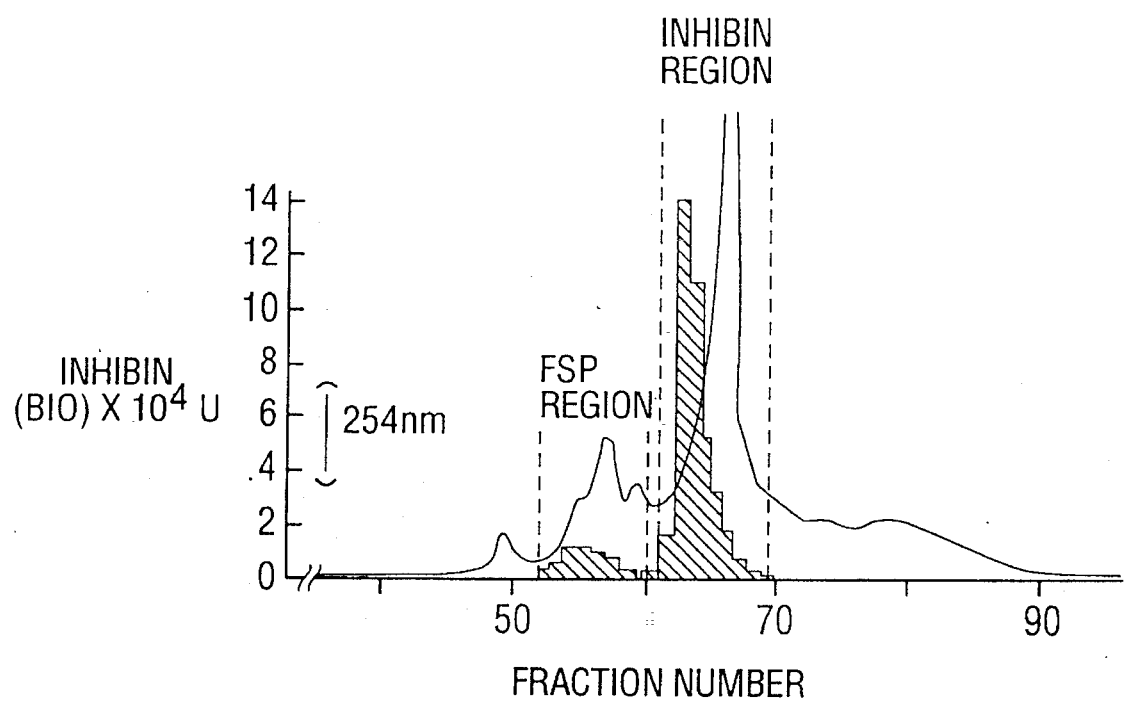
FIG. 1 depicts an RP-HPLC chromatogram showing RP-HPLC of bFF FSP containing fractions following gel permeation fractionation. FSP-containing fractions obtained from two successive gel permeation steps under neutral and acidic conditions were fractionated on an Ultrapore RPSC column using a 30 min linear gradient of 0–50% acetonitrile in 0.1% TFA. In the second panel, dashed lines refer to inhibin immunological activity determined with #749 antiserum and the solid line with #474 anti-serum. (See text for details).
Figure 1B:
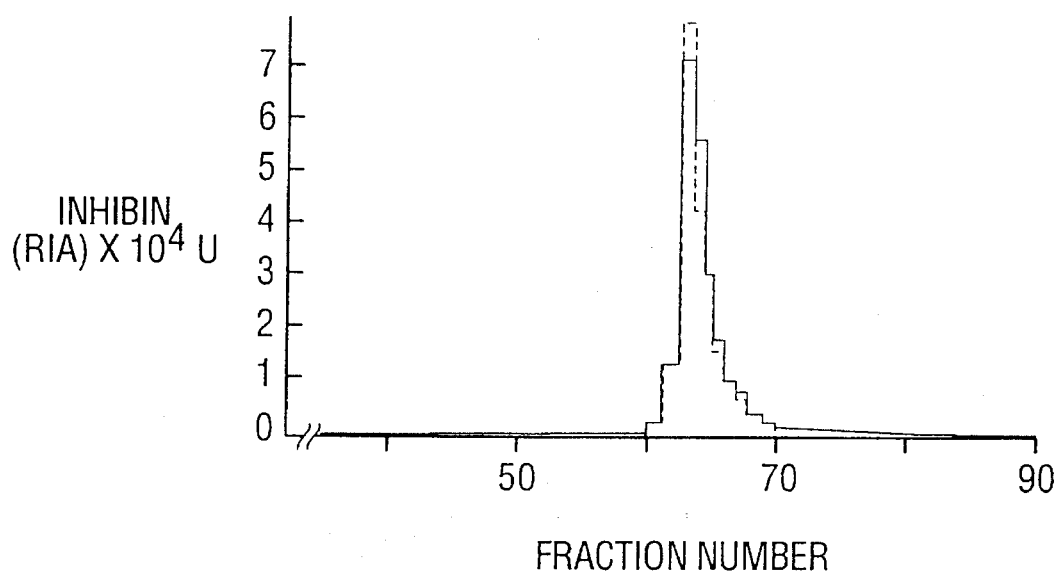

The protein separation methods employed were based on those previously described for the isolation of bovine 31 kD inhibin ]Robertson et al. (1986) Mol. Cell Endocrinol. 44 271–277]. Bovine follicular fluid was fractionated by gel permeation chromatography on Sephacryl S200HR (Pharmacia) in 0.05M ammonium acetate pH 7.0. Following a pH precipitation step, the void volume fractions were fractionated by gel permeation on Sephadex G100 (Pharmacia) in 4M acetic acid. The 31 kD inhibin-containing fractions were then separated by reversed phase HPLC (FIG. 1). FSH-suppressing activity located in fractions 52–60 eluted earlier than 31 kD inhibin (fractions 61–68). The FSP-containing fractions were rerun using a shallow 20–40% acetonitrile gradient in 0.1% TFA under similar reversed phase HPLC conditions based on change in gradient steepness factor. Samples were then fractionated on a 10% acrylamide SDS-PAGE system [Laemmli U.K. Nature (1970) 227 680–685] and the samples recovered from the gel by an electroelution step [Hunkapiller et al. Methods Enzymol. (1983) 91 227–236]. To remove SDS from the electroeluted samples, they (containing ca. 3% SDS) were diluted to a final concentration of 0.2% SDS with 0.1% TFA and applied to a Brownlee RP300 column (30×2.1 mm, Applied Biosystems Inc.) and fractionated on a 30 min 0–70% acetonitrile gradient in 0.1% TFA at 0.4 ml/min. Eluted samples were collected in siliconised tubes in the presence of 20 µl 0.02% SDS and lyophilized.

The amino acid sequence determination was performed using a gas/liquid phase model 470A sequencer (Applied Biosystems Inc.) and PTH-amino acids identified by HPLC [Zimmerman et al., Anal Biochem. (1977) 77 pp 569–573]. The protein sequence data base from Protein Identification Resource, NBRF, Georgetown University Medical Center was employed for assessment of sequence identities.

Pituitary cell cultures from adult male Spraque-Dawley rats were prepared as previously described [Scott et al., Endocrinology (1980) 107 pp 1536–1542]. Inhibin and FSP fractions were added on day two of culture and the media and cells separated on day five. FSH and LH were determined in media and cell lysates by RIA. Inhibin activity was determined by an in vitro bioassay method [Scott et al., (1980)] utilizing the above culture conditions with a bFF preparation as standard previously calibrated in terms of an ovine testicular lymph preparation.

The in vitro neutralization procedure [McLachlan et al., Mol. Cell Endocrinol. (1986) 46 pp 175–185] consisted of the incubation of a volume of an inhibin anti-serum with graded doses of inhibin or FSH-suppressing activity for 2 hours at 20° C. The samples were then added to the pituitary cell culture wells and the degree of neutralization calculated by comparing the dose-response lines in the presence or absence of various anti-sera concentrations.

Inhibin immunoactivity was determined using a second antibody radio immunoassay [McLachlan et al., (1986)] employing idoinated 31 kD inhibin as tracer and either an anti-serum (#474) raised against bovine 58 kD inhibin [McLachlan et al., (1986)] or an anti-serum (#749) raised against bovine 31 kD inhibin [McLachlan et al., J. Clin. Endocr. Metab. (1987)]. These methods showed minimal or non-detectable cross-reaction against bovine inhibin α and β subunits and a large range of growth factors [McLachlan et al., (1987)]. The standard employed was a partially purified 31 kD bovine inhibin preparation.

Isolation and Characterization bFF was fractionated by sequential gel permeation chromatography under neutral and acidic pH conditions followed by reversed-phase HPLC and preparative SDS-PAGE. FSH-suppressing activity associated with non-detectable inhibin immunological activity was identified in fractions eluting earlier than inhibin on reversed phase HPLC (FIG. 1). The combined FSP-containing fractions were separated by preparative SDS-PAGE and the activity electroeluted from the gel. Bioactivity was identified in varying proportions according to the batch, in the 31, 35 and 39 kD regions of the gel.

Figure 2:
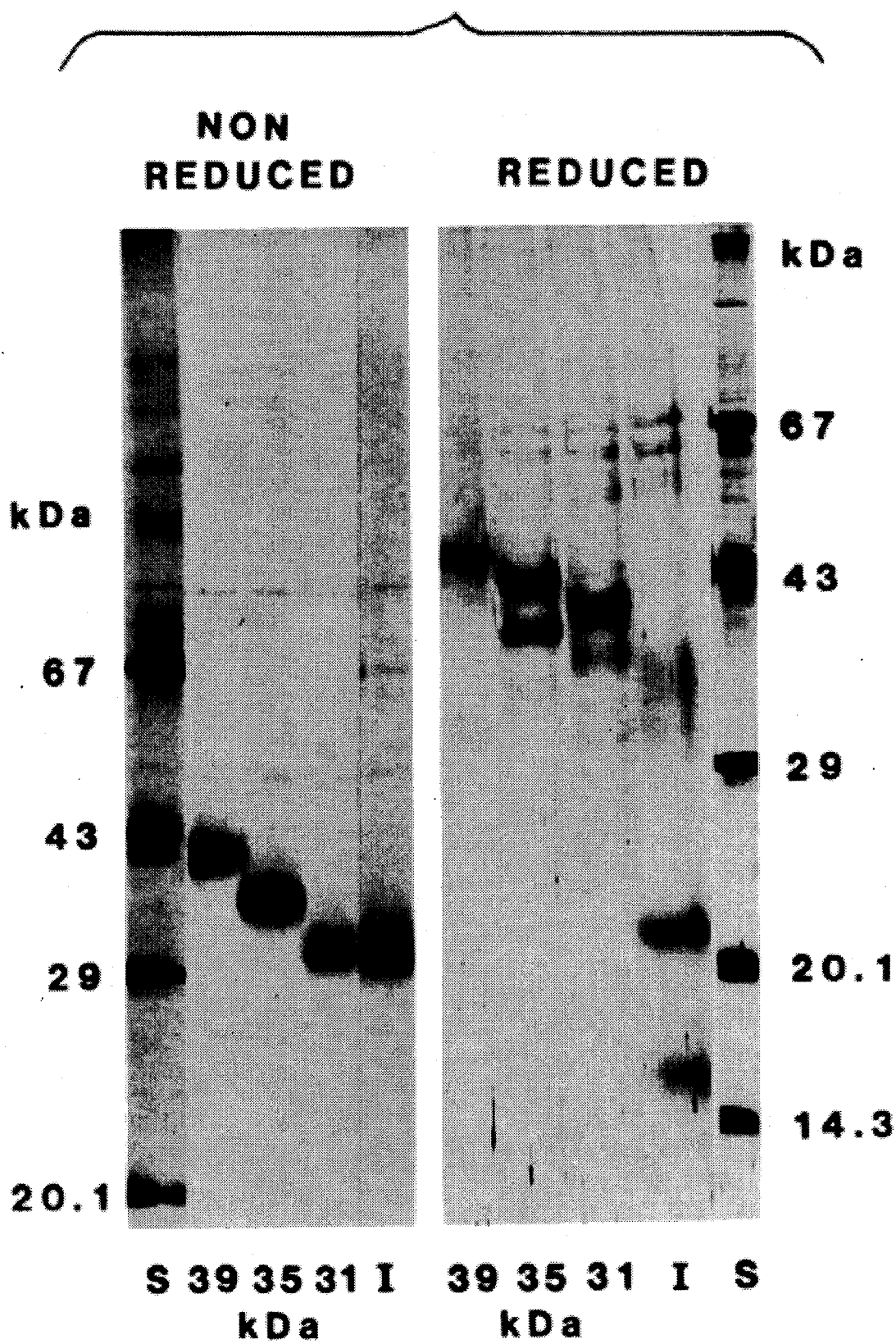
FIG. 2 depicts silver-stained analytical SDS-PAGs of purified preparations of 31, 35 and 39 kD FSP and bovine 31 kD inhibin. Samples were electrophoresed on 12.5% polyacrylamide gels and silver stained. Samples were reduced with β-mercaptoethanol. Molecular wt standards (S) bovine serum albumin 67000, ovalbumin 43000, carbonic anhydrase 29000, goose eggs lysozyme 20800, chick egg lysozyme 14300. I=bovine 31 kD inhibin.

Three bioactive polypeptides were isolated with molecular masses of 31, 35 and 39 kD as determined on SDS-PAGE (FIG. 2). Under reducing conditions, molecular masses of 45 kD, 42 and 39 kD, and 41 and 38 kD respectively, for the 31, 35 and 39 kD forms of FSP were obtained indicating that these polypeptides were probably a single chain structure with microheterogeneity arising from COOH-terminal truncation and/or glycosylation. All three polypeptides had identical NH$_2$-terminal amino acid sequences (Table 1) as deduced from automated Edman degradation.

TABLE 1

| FSP | Residues identified (Cycle Number) | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| 31kD | G | N | S/C | T | L | R | Q | A | K | N | G | — | — | Q | V | L | Y | K |
| 35kD | G | N | S/C | T/W* | L | R | Q | A | K | N | G | R | — | Q | V | L | Y | K |
| 39kD | (G) | N | S/C | — | L | (R) | Q | A | K | N | G | (R) | S/C | Q | V | L | Y | K |

*The assignment of threonine was ambiguous because the signal was lower than expected for the amount of protein sequenced.

Initial yields were 24, 160 and 20 pmol respectively. Bracketed amino acids were identified with less certainty. The major signal detected at cycle 3, 13 was in the position of the dithiothreitol adducts of PTH-serine and PTH-cystine. This signal, in the absence of an authentic PTH-serine signal suggested either a modified serine or a cysteine residue. The only contaminating sequences detected gave signals of 5 pmol or less in the case of the 35 and 31 kD analyses.

Figure 3A:
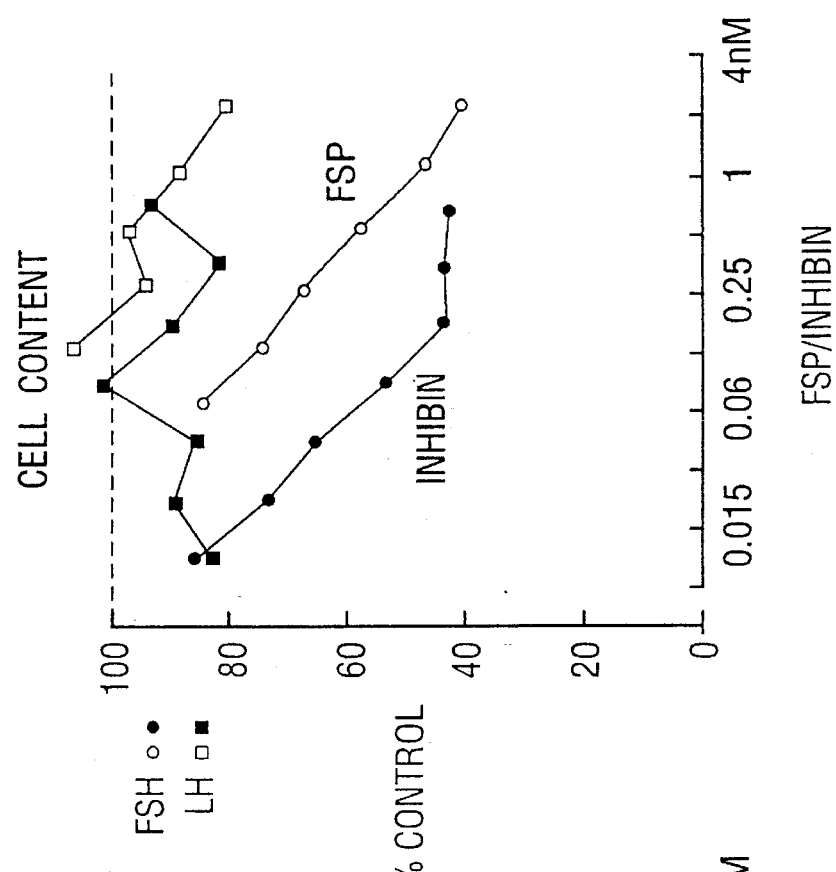
FIG. 3 illustrates the effect of FSP and inhibin on basal FSH and LH (media) release and cell content of cultured rat pituitary cells in vitro. The FSH media dose response lines for FSP and inhibin were non parallel. The corresponding dose response lines with FSH cell content were parallel.
Figure 3B:
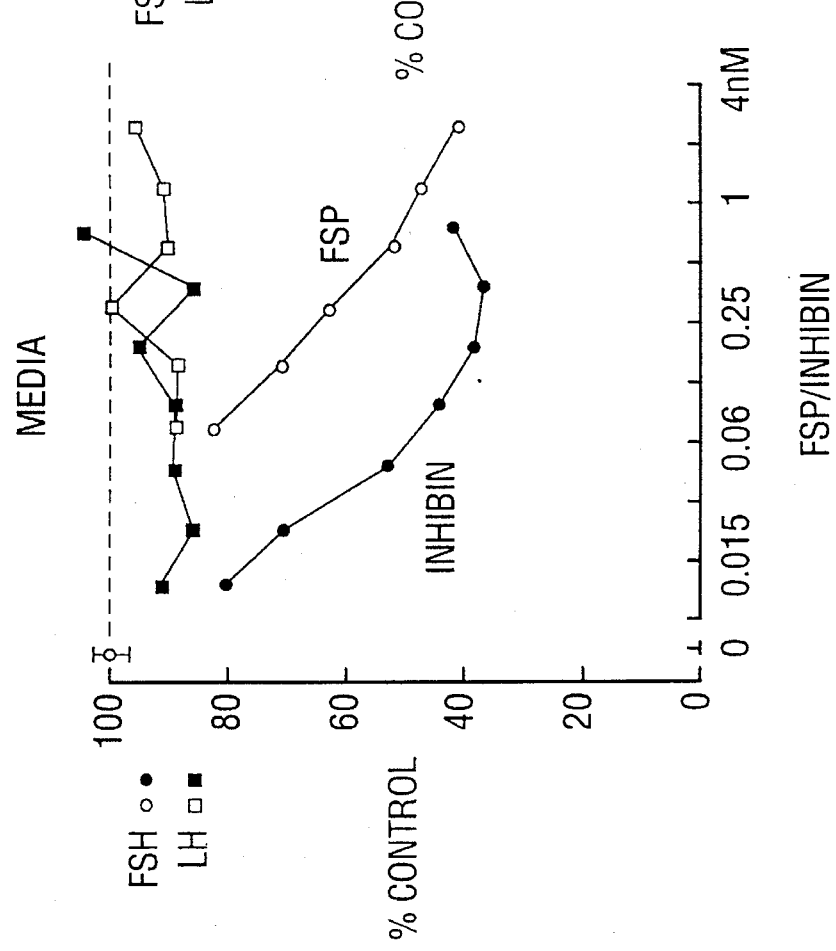

The inhibin-like biological activity of FSP was examined in a rat pituitary cell culture assay (FIG. 3). FSP suppressed basal FSH release (50% inhibitory concentration IC$_{50}$=0.18 nM) and FSH cell content (IC$_{50}$=0.22 nM) in a similar manner to inhibin although the FSH release dose-response lines were non-parallel. No dose related effects of FSP and inhibin was observed on basal LH release and LH cell content. Using the FSH cell content as a basis for a bioassay, FSP exhibited the following inhibin biological activities: 31 kD FSP, 89 U/µg protein; 35 kD FSP, 72 U/µg protein and 39 kD FSP, 35 U/µg protein. These specific activities are 5–10% that of bovine 31 kD inhibin (750 U/µg).

Accordingly, the protein has an inhibin-like bioactivity based on the ability to suppress FSH cell content of pituitary cells taking into account confidence limits within the methodology of Scott et al. (1980) between 27 U/µg and 114 U/µg. The range of bioactivities for the entire range of 30 kD to 60 kD proteins is between 27 U/μg and 300 U/μg.

The reactivity of bFSP in a previously described inhibin RIA system [McLachlan et al (1986) Mol. Cell. Endocr. 47, 175] was negligible. Consequently, the calculated biological:immunological ratio of bFSP is >320 whilst it is 0.35 for 31 kD bovine inhibin as determined using an anti-inhibin antiserum.

FSP inhibin like bioactivity was not significantly neutralized by an inhibin anti-serum in the in vitro neutralization assay in contrast to the neutralization of a maximally suppressed dose of 31 kD inhibin bioactivity.

The observation that some 39 kD FSP preparations contained a 35 kD protein suggest that 35 kD and perhaps 31 kD FSP are processed forms of 39 kD FSP.

FSP is not inhibin, nor contaminated inhibin, based on its different sequence, its molecular weight, absence of subunit structure, non-detectable inhibin immunological activity and the failure of inhibin anti-serum to neutralize FSP biological activity in vitro. [Robertson et al., (1986)].

The available amino acid sequence data for FSP shows no homology to inhibin but partial (40%) identity to a number of diverse proteins including phosphoenolpyruvate carboxylase, bovine intestinal calcium binding protein and human interferon α-1 precursor, of which only the latter protein demonstrated growth regulating activity. Although inhibin itself has not been shown to exhibit growth regulatory activity, other proteins structurally similar to inhibin [e.g. activin (inhibin β subunit dimer [McLachlan et al., Bailliere's Clin. Endocrinol. and Metab. (1987) 1 pp 89–112]), TGF-β [Roberts et al., Cancer Surveys (1985) 4 pp 683–705], Mullerian Inhibitory Substance [Cate et al., Cell (1986) 45 pp 685–698]] do so.

Further, due to the homology between FSP and human α interferon, it is interesting to note that it has been suggested that human α interferon interacts in vivo with the function of both FSH and LH. In a study involving normally cycling healthy women [Kauppila K. et al., Int. J. Cancer (1982) 29, 291–294] circulating concentrations of FSH and LH were not affected by interferon administration in contrast to serum sex steroids indicating that diminished serum steroid concentrations were not due to a decreased release and/or synthesis of FSH and LH. The results of the study suggest that interferon modulates the function of both FSH and LH by partially blocking their stimulatory action on ovarian steroidogenesis.

Human leukocyte-derived interferon has also been shown to exert an inhibitory effect on Leydig cell steroidogenesis in vitro [Grava et al (1985) Biochem. Biophys. Res. Commun. 127 809–815].

The inhibin-like in vitro biological activity of FSP showed a number of similarities with inhibin. For example, the FSH, but not LH, basal release and cell content were inhibited indicating the FSP can exhibit at least two actions, namely the ability to inhibit FSH release and to promote FSH degradation, activities which previously have been demonstrated with inhibin [Farnwork P. G. et al., Endocrinology (1987) in Press]. Using FSH cell content as an in vitro bioassay end point FSP is 5–10% as active as inhibin. Nonetheless it is still highly potent in vitro ($IC_{50}$=0.2 nM) suggesting that it may play an alternative physiological role in suppressing FSH.

EXAMPLE 2 a. Human FSP (hFSP)

Figure 4A:
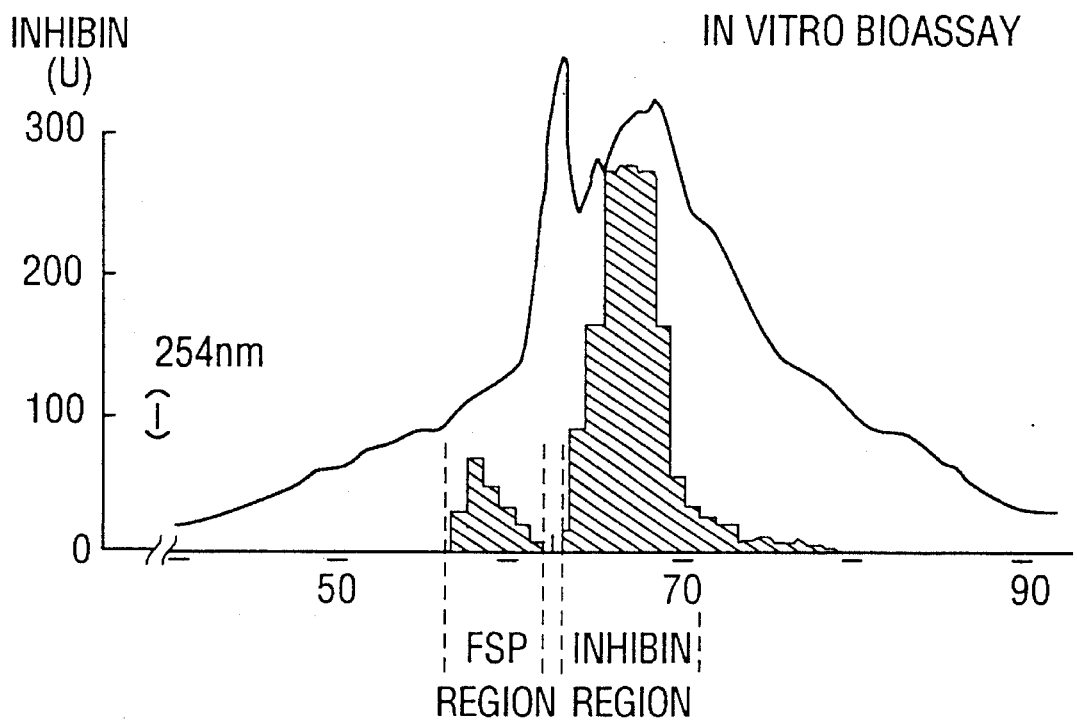
FIG. 4 illustrates RP-HPLC separation of hFSP bioactivity from hFF. See FIG. 1 for further details.
Figure 4B:
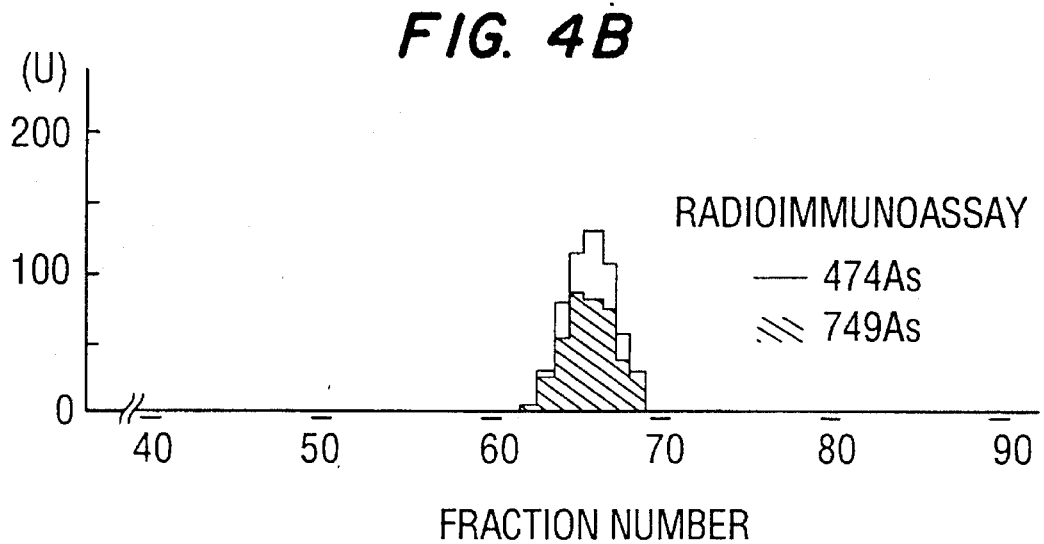

The presence of FSP in hFF was investigated using a similar approach to that used for the characterisation of FSP from bFF. In vitro bioactivity was located in fractions earlier eluting than inhibin in the reversed phase HPLC step used in fractionation of inhibin from hFF (FIG. 4). No detectable immunological activity was found associated with this region of FSH suppressing activity using inhibin radioimmunoassays which were used in identifying human inhibin in its purification from hFF. Fractionation of the bioactive fractions on preparative-PAGE resulted in the recovery of bioactivity in the 40–60 kD region of the gel with peaks of activity at 46 and 55 kD (FIG. 5). The molecular weight range of hFSP (40–60 kD) was in the upper range of that observed with bFSP (30–52 kD) but lower MW forms may also exist in low abundance and not be detected here. Alternatively, differences in glycosylation may account for some alterations in MW.

INDUSTRIAL APPLICATION

Uses of FSP

In International patent application No. PCT/AU85/00119 uses of inhibin were described. As discussed in this application FSP demonstrates similar biological activity to inhibin. It should be readily recognised that uses described in that application for inhibin will also apply to FSP.

FSP or parts thereof in accordance with the invention provide antigens which may be used as immunogens to immunise man or animals against endogenous FSP. One possible application is to elevate FSH titres and/or increase fertility.

FSP or derivatives thereof may be used as bioactive or therapeutic agents in man and in animals. One possible application is to depress circulating FSH titres and thus act as a contraceptive. Removal of FSP following administration may result in a rebound in FSH titres and thus increase fertility. FSP may be used in the treatment and diagnosis of cancers and may have applications as a growth factor or cell differentiation factor.

FSP or derivatives thereof may also be used in the diagnosis and treatment of fertility disorders.

We claim:

1. A substantially pure, single-chain protein derived from follicular fluid, said protein being characterized by:

a molecular weight of between about 30 kD and about 60 kD as estimated by SDS-PAGE in the absence of reducing agents;

an in vitro FSH-suppressing activity which is not inhibited by neutralizing inhibin anti-sera; and lack of inhibin immunoactivity.

2. The protein as defined by claim 1, having an NH$_2$— terminal amino acid sequence comprising substantially the sequence:

Gly—Asn—Ser—Trp—Leu—Arg—Gln—Ala—Lys—
Asn—Gly—Arg—*—Gln—Val—Leu—Tyr—Lys wherein * represents an unspecified amino acid at the position indicated.

3. The protein as defined by claim 1, having a molecular weight selected from the group consisting of about 31 kD and about 35 kD, as estimated by SDS-PAGE in the absence of reducing agents.

4. The protein as defined by claim 3, derived from bovine follicular fluid.

5. The protein as defined by claim 1, having a molecular weight of between about 40 kD and about 60 kD as estimated by SDS-PAGE in the absence of reducing agents.

6. The protein as defined by claim 5, having a molecular weight selected from the group consisting of about 46 kD and about 55 kD, as determined by SDS-PAGE in the absence of reducing agents.

7. The protein as defined by claim 1, wherein said protein is a glycoprotein.

8. A protein as defined in claim 1, wherein said protein has an inhibin-like bioactivity based on the ability to suppress FSH cell content of pituitary cells in culture of between 27 U/μg and 300 U/μg.

9. The protein as defined by claim 8, derived from human follicular fluid.

10. The protein as defined by claim 1, having a molecular weight of about 39 kD, as estimated by SDS-PAGE in the absence of reducing agents.

11. A substantially pure, single-chain protein derived from follicular fluid, said protein being characterized by:

a molecular weight of between about 30 kD and about 60 kD as estimated by SDS-PAGE in the absence of reducing agents;

an in vitro FSH-suppressing activity which is not inhibited by neutralizing inhibin anti-sera; and lack of inhibin immunoactivity, when produced by purification from natural sources, chemical synthesis, or recombinant DNA techniques.

12. A substantially pure, single-chain protein derived from follicular fluid, said protein being characterized by:

a molecular weight of between about 30 kD and about 52 kD as estimated by SDS-PAGE in the absence of reducing agents;

an in vitro FSH-suppressing activity which is not inhibited by neutralizing inhibin anti-sera; and lack of inhibin immunoactivity.

13. A substantially pure, single-chain protein derived from follicular fluid, said protein being characterized by:

a molecular weight of between about 30 kD and about 52 kD as estimated by SDS-PAGE in the absence of reducing agents;

an in vitro FSH-suppressing activity which is not inhibited by neutralizing inhibin anti-sera; and lack of inhibin immunoactivity, when produced by purification from natural sources, chemical synthesis, or recombinant DNA techniques.

14. A composition comprising at least one protein as defined by claim 1 together with a non-toxic carrier or diluent.

15. The composition as defined by claim 14, wherein said composition is suitable for oral administration.

16. The composition as defined by claim 15, wherein said composition includes a non-toxic adjuvant.

17. The composition as defined by claim 14, in injectable form.

18. The composition as defined by claim 17, wherein said composition includes a non-toxic adjuvant.

19. The composition as defined by claim 14, in sustained release form.

20. The composition as defined by claim 19, wherein said composition is suitable for implantation and sustained release in a vertebrate.

* * * * *